United States Patent [19]

Sepetka et al.

[11] Patent Number: 4,832,047
[45] Date of Patent: May 23, 1989

[54] GUIDE WIRE DEVICE

[75] Inventors: Ivan Sepetka, Mountain View; Erik T. Engelson, Palo Alto, both of Calif.

[73] Assignee: Target Therapeutics, Santa Monica, Calif.

[21] Appl. No.: 132,924

[22] Filed: Dec. 15, 1987

[51] Int. Cl.⁴ ............................................. A61H 25/00
[52] U.S. Cl. ..................................... 128/772; 128/657
[58] Field of Search .................... 128/772, 656–658, 128/341–344; 604/95, 170, 280–283

[56] References Cited

U.S. PATENT DOCUMENTS

| | | | |
|---|---|---|---|
| 4,538,622 | 9/1985 | Samson et al. | 128/657 X |
| 4,545,390 | 10/1985 | Leary | 128/657 X |
| 4,554,929 | 11/1985 | Samson et al. | 128/657 X |
| 4,616,653 | 10/1986 | Samson et al. | 128/657 X |
| 4,719,924 | 1/1988 | Crittenden et al. | 128/657 X |
| 4,724,846 | 2/1988 | Evans, III | 128/772 |

*Primary Examiner*—Max Hindenburg
*Assistant Examiner*—Angela D. Sykes
*Attorney, Agent, or Firm*—Peter J. Dehlinger

[57] ABSTRACT

A guide wire formed with a distal tapered segment and having a distal-end coil carried over a portion of the tapered segment. The strand forming the helical wrappings of the coil is reduced in thickness in the region of proximal attachment to the wire, to reduce the difference in diameter between the wire and the coil. Also disclosed is a method of producing the coil.

10 Claims, 2 Drawing Sheets

GUIDE WIRE DEVICE

FIELD OF THE INVENTION

The present invention relates to guide wires with distal-end coils, to improved coils for use with guide wires, and to methods of producing such coils.

BACKGROUND OF THE INVENTION

Flexible wires which can be guided by torquing into small-vessel sites in the body, such as along vascular pathways or ducts, have a number of uses in medicine. One important use is as a catheter guide wire. In this application, the wire typically is fed through the catheter lumen and the catheter and wire are guided as a unit, by wire torquing, toward the target site. If the target site is deep within a soft-tissue, and can be accessed only along a tortuous,,.small-vessel path, it is usually necessary to alternately advance the more flexible guide wire ahead of the catheter, then thread the catheter along the advanced portion of the wire. By first preshaping (curving) the guide wire tip, and by torquing the guide wire during catheter placement, the wire can be directed into side-branching vessels and the catheter can then be advanced over the wire into the branching vessel. When the target site is reached, the wire can be withdrawn to allow fluid material to be injected through the catheter.

The wire may also be used as a radio-opaque probe for use in localizing sites of pathology, such as tumor regions, within the body. Here the wire, equipped with a radio-opaque probe, is guided to the site of interest by radiographic imaging. Once the probe is in place, its location can be used for guiding the delivery of drugs into or focusing radiation at the site, or as a site marker for surgical excision. The probe may also be used as a microwave antenna, for producing localized heating at the probe site in response to microwaves directed at the probe. A wire of this type may also be used for dislodging or puncturing plaque deposit material in a vessel, or for purposes of making the vessel accessible to catheter entry and/or balloon placement in the region of plaque.

Torqueable wires which can be guided into small-vessel sites, along tortuous vessel paths, have been proposed heretofore. Typically, these wires are formed of flexible, torqueable filament material, such as stainless steel, and have preferred diameters between about 8–40 mils (thousandths of an inch). The wire may be provided with a bent distal tip, or a bent spring coil tip which can be oriented, by torquing the opposite end of the wire, to follow a desired pathway at a vessel branching. Ideally, torque transmission should be controlled, such that a selected amount of torquing produces a desired amount of wire rotation at the bent distal tip.

In order to achieve both good torqueability along the wire and good flexibility at the distal end region of the wire, for movement through tortuous, small-vessel pathways, guide wires having relatively large-diameter body portions and tapered distal end regions have been proposed, such as in U.S. Pat. No. 4,545,390. Typically in this type of wire, the body portion is up to 200 cm or more in length, and the tapered region, 5–50 cm or longer. The relatively large diameter of the body portion wire, e.g., 14–40 mils, reduces the possibility of wire twisting, shearing and/or deformation in response to a torque applied to the wire. At the same the relatively greater flexibility in the tapered segment facilitates wire movement through sharp-bend regions in small-vessel pathways.

The wire construction just described preferably includes a coil spring which encases a major portion of the tapered end region, typically terminating at the end of the wire. In this construction, the core wire serves to transmit torque to the guide wire tip for wire steering into side-branching vessels, to transmit axial forces, and to support the catheter. The coil functions to provide column strength to the guide wire tip, and to increase the surface area of the tip region, to reduce the stress of the wire tip in contact with a vessel wall. Where the coil is formed of platinum or gold or tungsten, the coil also serves to enhance the radio-opacity of the wire tip. The coil also presents a soft end to prevent vessel trauma. The coil is typically attached as by brazing or soldering to the wire at the wire's distal tip and at the proximal end of the coil. It can be appreciated that the point of attachment of the spring coil to the wire, at the coil's proximal end, creates a step in the axial profile of the tapered wire region. Potentially this step creates a source of roughness which can injure vessel lining, and also become caught at the distal opening of the catheter, as the guide wire is withdrawn from the catheter. The latter may cause the coil to be pulled off the wire, particularly since the attachment of the coil to the wire at the step tends to be weak for lack of common bonding area between the coil and wire. The difference in coil and wire diameter at the coil end can be reduced by forming a reduced-diameter step in the wire, to accommodate the added thickness of the coil. However, the step in the wire creates a zone of poor torque transmission, and also allows sharp wire bending to occur.

SUMMARY OF THE INVENTION

It is one object of the invention to provide, in a flexible wire with an end coil, an improved spring coil which largely solves or avoids problems encountered with prior art guide-wire coils.

A more specific object of the invention is to provide such a coil which substantially reduces the difference between the diameter of the wire and the diameter the coil at the point of attachment of the coil to the wire.

Another specific object of the invention is to provide such a coil having increased surface contact with the wire at the point of proximal attachment.

It is still another object of the invention to provide a method of producing such coil which allows high-volume production.

The present invention is an improvement on a wire device composed of a torqueable wire having a distal-end segment terminating at a distal tip region, and a spring coil attached to and encasing a portion of the distal end segment. The coil is composed of helical wrappings of a wire strand, and is attached to the wire at the wire's distal tip region, and in a zone of substantially constant diameter or continuously decreasing taper within the distal-end segment. In the improvement, the strand forming the coil has a substantially fixed-dimension cross section in the portion of the coil extending between the wire's distal end and the zone of coil attachment, and a progressively reduced-diameter cross-section on extending proximally along this zone. The difference between the diameter of the wire and the diameter of the coil in the coil-attachment zone is thus progressively reduced along the zone in a proximal direction.

Preferably, the total wire length is between about 50-300 cm, the distal-end segment is tapered along its length, the total length of the distal segment is between about 5-50 cm, and the zone of attachment of the coil to the wire is in a tapered portion of the distal tip region. The strand material making up the coil is preferably a platinum or stainless steel wire having a circular cross section of between about 2-10 mils, and the wire thickness, at the most reduced-thickness portion of the coil, is less than about 25-50% of the normal circular cross section.

In one embodiment, the reduced-thickness coil strand is progressively more flattened on its inner surface (the surface in contact with the wire), or on both its inner and outer surfaces. The flattened cross-sections of the strand in the zone of attachment provides progressively greater surface contact between the strand and the wire. Therefore, where the coil is attached to the wire by a bonding material, such as brazing or solder, the bonding between the wire and coil is increased.

Also forming part of the invention is the improved coil having flattened strand windings in a proximal region thereof, such that the wall thickness of the coil is reduced on progressing along the proximal region toward the proximal end of the coil.

In another aspect, the invention includes a method of forming a helical coil designed for attachment, at one coil end, to a zone of substantially constant diameter or continuous taper within the distal-end segment of the flexible, torqueable wire. The method includes wrapping a wire strand helically on a rotating mandrel. At the end region of the coil adjacent said one coil end, the strand being wrapped is progressively reduced in thickness, preferably by progressive flattening, on progressing toward this end.

These and other objects and features of the present invention will become more fully apparent when the following detailed description of the invention is read in conjunction with the accompanying drawings.

DETAILED DESCRIPTION OF THE INVENTION

A. Guide Wire Device

Figure 1:
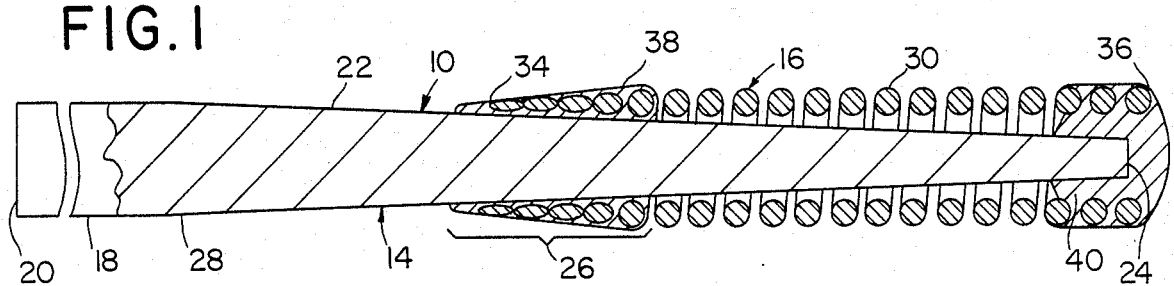
FIG. 1 is a sectional view showing opposite end regions of a wire device constructed according to a preferred embodiment of the invention.

FIG. 1 shows a wire device 10 constructed according to the invention. The device includes a flexible, torqueable core wire 14, and a coil 16 which is carried on and encases a distal end portion of the wire.

In one general embodiment, the wire device is used as a catheter guide wire for accessing a target site which is reached typically by wire movement along a tortuous, narrow-vessel path, for example, through a soft tissue region which contains the target site. Such a wire device can be used for guiding a catheter to the site, or for probing the target site, for example, for localizing the target site radiographically, or for heat generation at the target site in response to microwaves. Although the device which will be detailed herein is constructed specifically for movement through a small-vessel tortuous vessel pathway, it will be understood that wire devices constructed for applications in which different flexibility or column-strength characteristics are required can be similarly constructed.

Wire 14 is a flexible torqueable guide wire having a total length between about 50-300 cm, and a maximum diameter of the wire between about 8-40 mils (thousandths of an inch). The wire has a relatively long, body portion 18 which terminates at a proximal end 20, and a relatively short distal-end portion or segment 22 which terminates at a distal end 24. The body portion preferably has a substantially constant diameter along its length, but may contain regions of wire taper. The distal end portion is preferably tapered along its entire length. The boundary between the two wire portions is indicated at 28.

The distal portion of the wire contains a zone 26 of substantially continuous taper where the proximal end of the coil is attached to the wire. This zone is typically located between boundary 28 and distal end 24, and preferably in a tapered region of the distal portion. Alternatively, zone 26 may be directly adjacent the body portion, and/or in a constant diameter region of the distal portion.

In a preferred embodiment of the device, the tapered distal portion is between about 5-50 cm in length, and preferably about 15-20 cm in length, with the body portion making up the remainder of the wire length. It will be appreciated that only a small part of the body portion is shown in the figure. In a preferred embodiment, the distal-end segment has a continuous taper along its length, and the taper is preferably such as to reduce the wire diameter in the wire from about 8-40 mils at boundary 28 to a minimum diameter of typically 1-5 mils at the distal wire end.

The guide wire may be formed from flexible metal wire having a length typically between about 50-300 cm and a selected diameter between about 8-40 mils. Stainless steel wire of this type are commercially available, such as from Wytech and National Standard.

The distal end segment of the wire may be tapered by wire grinding, drawing, or etching techniques. The advantages of the grinding method are accurate control over the depth of cut along the wire, and the ability to produce the continuous taper at any region along the length of the wire.

Etching techniques for etching stainless steel substrates are known. In forming the guide wire of the invention, the region or regions to be tapered are submerged in a chemical etching bath. The wire is gradually withdrawn from the bath at a rate which exposes submerged portions of the wire to greater etching add therefore greater reduction in wire diameter. The rate of wire removal can be adjusted to produce linear, concave, or convex tapers. The etching method has the advantage that many wires can be processed in single batch. Also, complex machining and or wire processing devices are avoided.

Wire drawing, in which a heated wire is drawn under tension to a desired diameter, can also be used to produce long regions of continuous taper in the wire. In this method, the selected region of wire is heated, for example within a firing oven, and drawn out at a preselected tension when a selected wire temperature is reached. By careful monitoring of wire temperature and temperature uniformity in the heated wire region, and rate of wire drawing, accurate continuous taper can be produced.

As indicated above, the wire device is designed primarily for use as a catheter guide wire, either for use alone in accessing a internal body site or, more commonly, in combination with a catheter for use in catheter placement at a target site. To this end, the wire may be equipped with a proximal guide member (not shown) for applying torque to the wire as it is being guided to a target site. Such guide members may include a torquing arm fixed to the guide wire, or a torquing wheel which limits the extent of rotational movement which can be applied.

Figure 2:
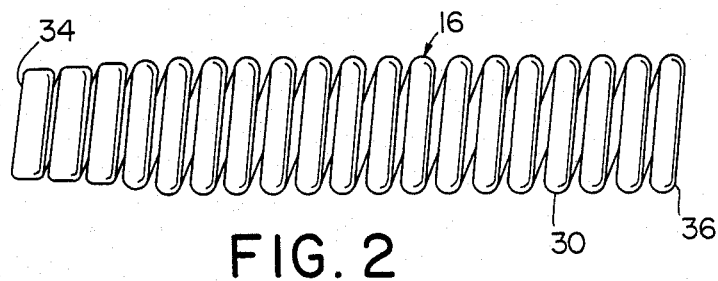
FIG. 2 shows the coil in the FIG. 1 wire device.

With reference to FIGS. 1 and 2, coil 16 is formed by helical wrappings of a wire strand 30. As seen in FIG. 1, the coil is attached at its proximal end 34 to the wire along zone 26, and adjacent its distal end 36, to the distal end of the wire. Preferably the coil terminates at the distal end of the wire device, as illustrated in FIG. 1. The coil length can range from a few cm up to the entire length of the distal-end portion, which may be 40 cm or more. Typically, the coil is between about 3–15 cm in length.

The inner diameter of the coil is such as to allow the coil to encase a selected portion of the wire's distal end region, as shown in FIG. 1. Typical the coil has an inner diameter of between about 5–20 mils. Alternatively, the inner diameter of the coil may be tapered, for example, to match the taper in the encased portion of the guide wire.

According to an important feature of the invention, the strand forming the coil has a substantially fixed-thickness, cross-section along a distal portion of its length, and a progressively reduced-thickness cross-section on extending proximally along the wire region corresponding to the zone of attachment. Typically the distal portion is longer than the proximal portion containing the progressively reduced thickness wire. The progressive thickness reduction of the wire is such as to progressively reduce the wall thickness of the coil on progressing toward the coil's proximal end, i.e., progressively reduce the difference between the diameter of the wire and the outer diameter of the coil, in the zone of coil attachment to the wire. As can be appreciated from FIG. 1, this feature significantly reduces the step in wire diameter at the proximal end of the coil.

The strand forming the coil is preferably a platinum, gold or tungsten wire having a circular cross-sectional diameter of between about 21–10 mils and a maximally reduced thickness, at the coil's proximal end, of between about 0.5–2.5 mils, i.e., between about 25–50% of the coil's normal circular thickness. Likewise, the width of the coil strand increases progressively, as seen best in FIG. 2. Methods for forming the coil, according to one aspect of the invention will be described below.

Attachment of the coil to the wire is by two or three solder or weld joints, including a proximal joint 38 in the zone of attachment of the wire, a rounded distal joint 40, and optionally, an intermediate joint (not present in the FIG. 1 embodiment) which may be about 1–3 cm from the distal end of the wire and coil. The intermediate joint can serve to transmit torque in the wire to the coil, to cause the end region of the coil (and wire) to bend slightly at the solder joint, allowing the wire to be guided in a selected direction in a vessel network by torquing the proximal end of the wire.

Considering the proximal joint, it can be appreciated from FIG. 1 that the flattening in the coil windings acts both to (a) increase the number of helical windings which are in contact with the wire, without distorting the inner diameter of the coil, and (b) increase the surface contact between the windings and the wire. As a consequence, the bonding between the coil and wire in the zone of attachment is improved over the bonding possible in a conventional coil.

Figure 3:
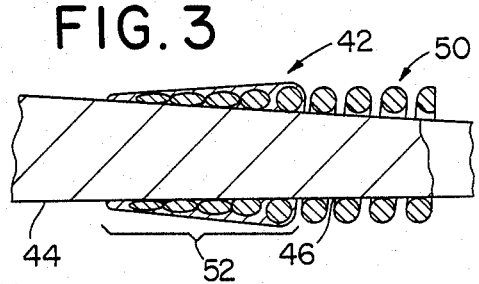
FIG. 3 shows the distal end region of a wire device having a coil formed according to another embodiment of the invention.

FIG. 3 shows the distal end region of a wire device 42 formed according to a second embodiment of the invention. A wire core 44 in the device has a tapered distal region 46, and a coil 50 which is attached to the wire at a zone of attachment 52 in the distal region. Like coil 16, the coil in the present embodiment has a major proximal section formed of a fixed-thickness strand having a circular cross-section, and a shorter distal region in which the strand is progressively flattened toward its proximal end. The coil differs from coil 16 in that the strand is flattened on its inner side only, giving a cap-shaped cross-section to the strands. The coil strand have a planar inner surface in their flattened region, providing greater surface contact between the coil and core wire in the zone of attachment.

Figure 4:
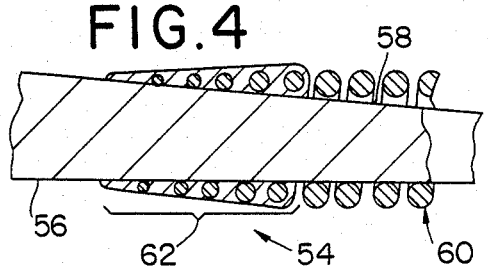
FIG. 4 shows the distal end region of a wire device having a coil formed according to still another embodiment of the invention.

FIG. 4 shows the distal end region of a wire device 54 formed according to still another embodiment of the invention. A wire core 56 in the device has a tapered distal region 58, and a coil 60 which is attached to the wire at a zone of attachment 62 in the distal region. The coil in the present embodiment has a major proximal section formed of a fixed-thickness strand having a circular cross-section, and a shorter distal region in which the strand is progressively flattened toward its proximal end, similar to above coils 16 and 50. The coil differs from these coils in that the reduced thickness in that the strand forming the coil is produced by thinning the wire with stretching, rather than by wire flattening. Thus the coil strand maintains its substantially circular cross-section throughout the coil, but has a gradual reduction in diameter progressing toward the coil's proximal end.

B. Method of Forming the Coil

Figure 5:
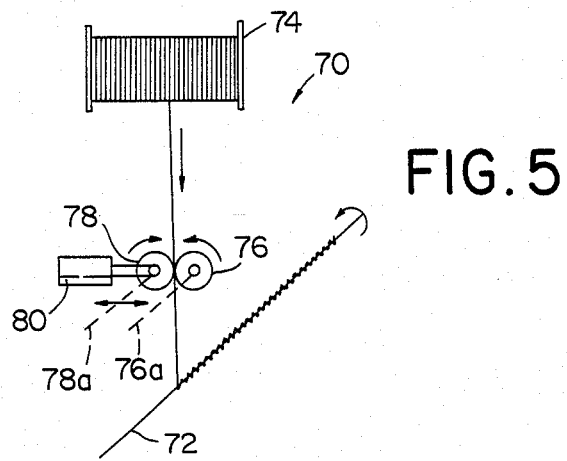
FIG. 5 illustrates the method of the invention used for producing a coil of the type shown in FIG. 2.

FIG. 5 illustrates a system 70 for forming a coil, such as coil 16, according to the method of the invention. The system generally includes two relatively movable subsystems. The first subsystem supports a wire mandrel 72 on which the coil is wrapped. Thus the mandrel has the same diameter as the desired inner diameter of the coil. The mandrel is supported for rotation about its long axis, and may be stabilized along its length by a series of posts (not shown) which confine the mandrel to a substantially linear axis, while allowing free wire rotation. One end of the mandrel is secured in a chuck or the like for rotation at a speed preferably between about 50–500 rpm.

The second subsystem is mounted for movement along the axis of the mandrel at a controlled translational speed which is determined by the rotational speed (wrapping speed) of the mandrel and the desired helical pitch of the coil. A conventional worm drive or stepper motor device may be used for advancing the subsystem at the required speed.

The second subsystem includes a spool 74 containing the coil strand material, and a pair of rollers 76, 78 which serve as a guide for the strand during coil formation, and also function to flatten the wire progressively at selected intervals during the wrapping operation. As seen in FIG. 5, the two rollers are mounted for rotation about parallel axes 76a, 78a, respectively, which are also parallel to the mandrel's long axis. In the embodiment illustrated in this figure, the rotational axis of roller 76 is fixed, while that of roller 78 is mounted on the piston end of a cylinder 80. This cylinder is operable to place position the roller a selected distance from roller 76. Preferably one of the rollers, such as roller 76, is driven for rotation at a speed which advances the strand through the rollers at the same rate that the coil strand is wrapped on the mandrel.

The operation of the chuck which rotates the wire, the drive system which advances the second system, the motor(s) which rotates one or both of the rollers for feeding the strand, and cylinder 80 which determines the clearance between two rollers is controlled by a microprocessor or the like whose operation will be apparent from the following description of the functioning of the coil-forming system.

Initially the second subsystem, and more specifically, the strand-feed region defined between the two rollers, is moved to a desired initial wrapping position along the mandrel. The coil strand is fed through the rollers, which are spaced to contact, but not deform the strand as it is advanced through the rollers. With the strand fastened to the mandrel, the mandrel is now rotated to begin the wrapping of the strand on the wire. At the same time, the second subsystem begins to advance slowly along the mandrel to produce a desired helical spacing of the strand wrapping on the mandrel. Alternatively, the second subsystem may be stationary, and the mandrel may be advanced slowly with the first subsystem. Preferably the coil is formed under wrapping conditions which produce a close-pack coil spacing in which the adjacent helical windings are in contact or nearly in contact with one another, as illustrated in FIG. 2.

When the length of the wrapped coil reaches a specified length (which is shorter than the final length of a coil) cylinder 80 is actuated to reduce the clearance between the two rollers progressively, to cause progressive flattening of the strand as it moves through the rollers. The point of initial strand compression on the mandrel is indicated at $b_i$ in FIG. 6. This progressive flattening is continued until a maximum coil flattening is achieved, typically within 2-5 coil windings of when strand flattening first begins. At this point, the cylinder is actuated to place the two rollers at their initial position which relieves the compression on the coil strand. This point, which corresponds to the beginning of the next-in-series coil on the mandrel, is indicated at $a_{i+1}$ in FIG. 6. The wrapping is continued under non-compression conditions until the tapered region of this next coil is reached ($b_{i+1}$), at which point the cylinder is again actuated for strand flattening. This procedure is repeated until a suitable wrapping length along the mandrel is reached.

Figure 6:
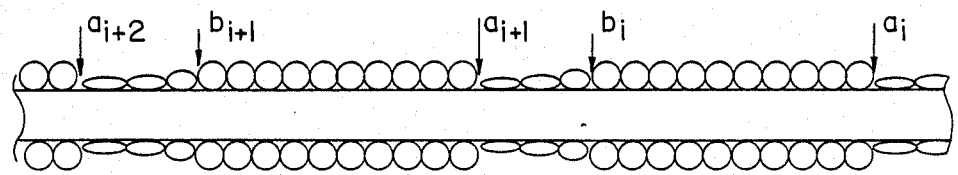
FIG. 6 is an enlarged fragmentary view of the mandrel and coils being formed on the mandrel in the FIG. 5 method.

With continued reference to FIG. 6, the individual coils are formed by cutting the winding at the point at or adjacent the point of maximum strand flattening (points $a_j$), and removing the coils from the mandrel.

Figure 7A:
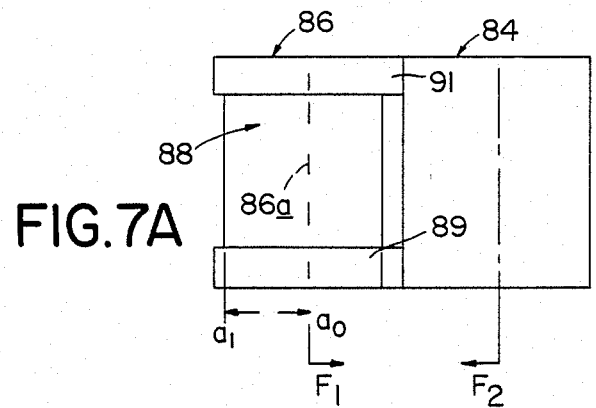
FIGS. 7A and 7B show top and side views of a pair of rollers use in a device for flattening coil strands in the method illustrated in FIG. 5.
Figure 7B:
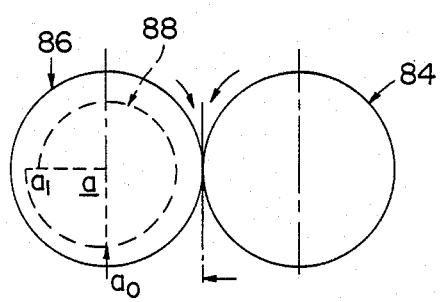

FIGS. 7A and 7B show top and side views, respectively, of a pair of rollers 84, 86 for use with the system illustrated in FIG. 5. The two rollers are mounted for rotation about fixed rotational axes at the centers of the rollers, such as the center 86a of roller 86. In this embodiment, the strand compression action of the rollers is produced by a cam surface 88 formed on a portion of the outer surface of the roller. This cam surface extends over a radial angle a and has a progressively greater diameter on extending from surface points $a_0$ to $a_1$ which define angle a. This angle is typically between about 10-90 degrees. The difference between the radial projection of the cam surface and the circular profile of the roller defines the extent of flattening of the circular cross section of the strand. One of the two rollers, such as roller 84, may be driven for rotation at a speed corresponding to the wrapping speed of the strand on the mandrel, as above. Tee two rollers are held in fixed relative positions by annular rings 89, 91 on either end of roller 86, as shown.

In a typical operation used in forming coils, according to this embodiment of the invention, the wire strand is fed between the two rollers, where the wire is engaged, but not flattened by the rollers. The wire is now fed onto the rotating mandrel, with translation of the two roller and the strand spool on the second subsystem forming a helical coil on the mandrel. Over the surface portion of roller 86 which is outside of points $a_0$, $a_1$, the coil strand is fed onto the mandrel without wire compression, forming the portion of the coil which is proximal to its flattened portion. As the strand is fed over the cammed portion of roller 86, the strand is progressively compressed between the two roller surface, producing the flattened portion of the coil. Immediately after the coil has been maximally flattened, the wire is out of contact with the cammed surface, and the strand again assumes the circular cross section which will mark the beginning of the next-in-series coil being formed on the mandrel.

The resultant coil winding has the appearance of the winding shown in FIG. 6, where the coil windings between each $a_j$ and the corresponding (left adjacent) $b_j$ points are produced during coil passage through the non-cammed surface of the rollers, and the flattendd region, by passage through the cammed region of the rollers. The individual coils are formed by cutting the windings at each point $a_j$ as above. The coils are attached to the tapered end regions of core wires, by brazing, soldering, or the like, as detailed above.

Figure 8:
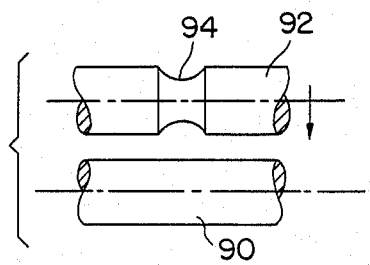
FIG. 8 shows a pair of rollers used in a device for producing the coil illustrated in FIG. 3.

FIG. 8 shows a pair of rollers 90, 92 which are used in place of rollers 76, 78 in the system shown in FIG. 5 for producing coils like coil 50 seen in FIG. 3. Roller 92 includes an annular groove 94 which is dimensioned to accommodate an outer surface portion of the wire being fed between the rollers, with the wire's inner surface being pressed against the cylindrical surface of roller 90. The rollers preferably are formed of or coated with tungsten carbide. As the two rollers are moved closer to one another, the coil strand's inner surface is progressively flattened, with little or no deformation of the outer surface. The operation and control of the rollers is substantially as described with reference to FIG. 5.

Methods for producing the wire thinning or stretching, in a system for producing a coil like coil 60 seen in FIG. 4, are available. In one method, the coil strand is wound on the mandrel under tension, with intermittent heating being used to stretch or thin the portions of the strand used to form the reduced-thickness region of the coils. In another method, the coil strand is prestretched under tension at regular intervals along its length, corresponding to those sections of the strand which will form the reduced-thickness regions of the coils.

From the foregoing, it can be appreciated how various objects and features of the invention are met. The novel wire device construction described herein provides the known advantages of a soft guidable tip, and enhanced column strength in a tapered guide wire. In addition, the present construction avoids the sharp step at the proximal end of the coil, and the potential problems of vessel trauma, and wire snagging in a catheter which are associated with a coil step. Another advantage of the invention is the increased area of contact of the coil with the wire at the proximal coil end, allowing an improved weld or bonding in this region. The improved bonding also cooperates with the reduced coil step to prevent the coil from being detached at its proximal joint by snagging.

The coil is easily formed, according to another aspect of the invention, by a continuous winding method which intermittently produces relatively short stretches of flattened-strand windings. Alternatively, a length of coil strand may be prestretched or flattened at selected intervals along its length, for producing the coils by simple coil winding methods.

While preferred embodiments of the invention have been described herein, it will be recognized that a variety of changes and modifications can be made without departing from the invention.

It is claimed:

1. A wire device comprising a flexible, torqueable wire having a proximal end and a distal-end segment terminating at a distal tip region, and a spring coil (i) formed by helical wrappings of a wire strand and (ii) attached to the wire at the wire's distal tip region and in a zone of substantially constant or continuously decreasing diameter within the distal end region of the wire, wherein the improvement comprises the strand forming the coil having a substantially fixed thickness cross section in a portion of the coil extending between the wire's distal end segment and said zone of coil attachment, and having a progressively reduced-thickness cross-section extending proximally along said zone, such that the difference between the diameter of the wire and the diameter of the coil in said zone is progressively reduced along said zone in a proximal direction.

2. The device of claim 1, wherein the progressively reduced-thickness cross-section of the strand in said zone provides progressively greater surface contact between the strand and the wire, and the coil is attached to the wire by a bonding material in said zone of attachment.

3. The device of claim 1, wherein the distal-end segment of the wire is a tapered segment having a length between about 3–50 cm.

4. The device of claim 3, wherein the wire has a proximal non-tapered portion which has a diameter of between about 8–40 mils and the minimum diameter of the wire, in the tapered region, is between about 1–5 mils.

5. The device of claim 1, wherein the coil strand has a circular cross section of between about 2–10 mils, and a minimum reduced-thickness cross-sectional thickness of between about 25–50% of the fixed-thickness cross section.

6. The device of claim 1, wherein the coil strand is a platinum, gold, or tungsten wire strand.

7. The device of claim 1, wherein the distal end segment is tapered along said zone of attachment, and the reduction in the wall thickness of the coil along this zone corresponds approximately to the change in wire diameter along the zone.

8. A spring coil formed by helical wrappings of a wire strand and characterized by (a) an inner diameter which is dimensioned to allow the coil to be placed on and encase a distal portion of a distal-end segment of a guide wire having a zone of constant or continuously decreasing diameter, (b) a relatively long distal region in which the strand forming said wrappings has a substantially fixed-thickness cross section, and (c) a relatively short proximal region in which the strand forming said wrappings has a progressively reduced-thickness cross section progressing proximally along the region of the coil, such that the wall thickness of the coil in said proximal region is progressively reduced along said region in a proximal direction.

9. The coil of claim 8, wherein the coil strand has a circular cross section of between about 2–10 mils, and a minimum reduced-thickness cross-section of the strand is between about 25–50% of the fixed cross-sectional thickness.

10. The coil of claim 8, wherein the coil strand is a platinum, gold, or tungsten wire strand.

* * * * *